United States Patent
Liu et al.

(10) Patent No.: US 10,183,973 B2
(45) Date of Patent: Jan. 22, 2019

(54) SOLVATE OF CYCLIC PEPTIDE COMPOUND, PREPARATION METHOD FOR SAME, AND USES THEREOF

(71) Applicant: SHANGHAI TECHWELL BIOPHARMACEUTICAL CO., LTD, Shaghai (CN)

(72) Inventors: Shidong Liu, Shanghai (CN); Xiusheng Wang, Shanghai (CN); Xiaoming Ji, Shanghai (CN)

(73) Assignee: SHANGHAI TECHWELL BIOPHARMACEUTICAL CO., LTD., Shanghai (CN)

( * ) Notice: Subject to any disclaimer, the term of this patent is extended or adjusted under 35 U.S.C. 154(b) by 0 days.

(21) Appl. No.: 15/314,458

(22) PCT Filed: May 29, 2015

(86) PCT No.: PCT/CN2015/080232
§ 371 (c)(1),
(2) Date: Nov. 28, 2016

(87) PCT Pub. No.: WO2015/180682
PCT Pub. Date: Dec. 3, 2015

(65) Prior Publication Data
US 2017/0198012 A1    Jul. 13, 2017

(30) Foreign Application Priority Data
May 29, 2014    (CN) .......................... 2014 1 0235521

(51) Int. Cl.
| | | |
|---|---|---|
| A61K 38/12 | (2006.01) | |
| C07K 7/56 | (2006.01) | |
| C07K 1/02 | (2006.01) | |
| C07K 1/30 | (2006.01) | |
| A61K 38/00 | (2006.01) | |

(52) U.S. Cl.
CPC ............... *C07K 7/56* (2013.01); *A61K 38/12* (2013.01); *C07K 1/02* (2013.01); *C07K 1/306* (2013.01); *A61K 38/00* (2013.01)

(58) Field of Classification Search
None
See application file for complete search history.

(56) References Cited

U.S. PATENT DOCUMENTS 8,980,827 B2    3/2015 Hong et al.

FOREIGN PATENT DOCUMENTS

| CN | 102614491 A | 8/2012 | |
| WO | WO-2012152225 A1 * | 11/2012 | ............... C07K 7/56 |

OTHER PUBLICATIONS

International Search Report dated Aug. 14, 2015 corresponding to International Patent Application No. PCT/CN2015/080232, filed on May 29, 2015, 2 pages.

* cited by examiner

*Primary Examiner* — Lianko G Garyu
(74) *Attorney, Agent, or Firm* — Mintz, Levin, Cohn, Ferris, Glovsky and Popeo, P.C.

(57) ABSTRACT

Provided in the invention is a solvate of a cyclic peptide compound, represented by formula I is the structural formula of the cyclic peptide compound, and, also disclosed are a preparation method for same and uses thereof.

Formula I

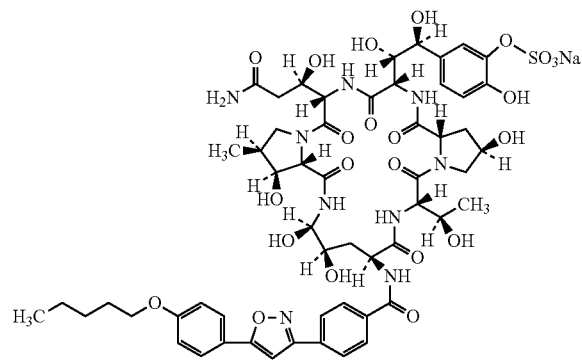

22 Claims, 10 Drawing Sheets

SOLVATE OF CYCLIC PEPTIDE COMPOUND, PREPARATION METHOD FOR SAME, AND USES THEREOF

TECHNICAL FIELD

The present invention relates a solvate of micafungin sodium water as well as preparation methods and uses thereof.

BACKGROUND

Micafungin is a novel anti-fungal drug of pneumocandins, and it inhibits the synthesis of the main ingredient of fungi cell walls, i.e. β-1,3-D-dextran, and therefore destroy the structure of fungal cells, thus leading to cytolysis. Micafungin is widely used for treating various infections, such as infections caused by *Aspergillus, Candida, Cryptococcus, Mucor, Actinomyces, Histoplasma, Dermatophytes* and *Fusarium* and the like.

Micafungin Sodium (also named as FK463) is the active pharmaceutical ingredient of Mycamine. The chemical structure of micafungin Sodium is shown as follows:

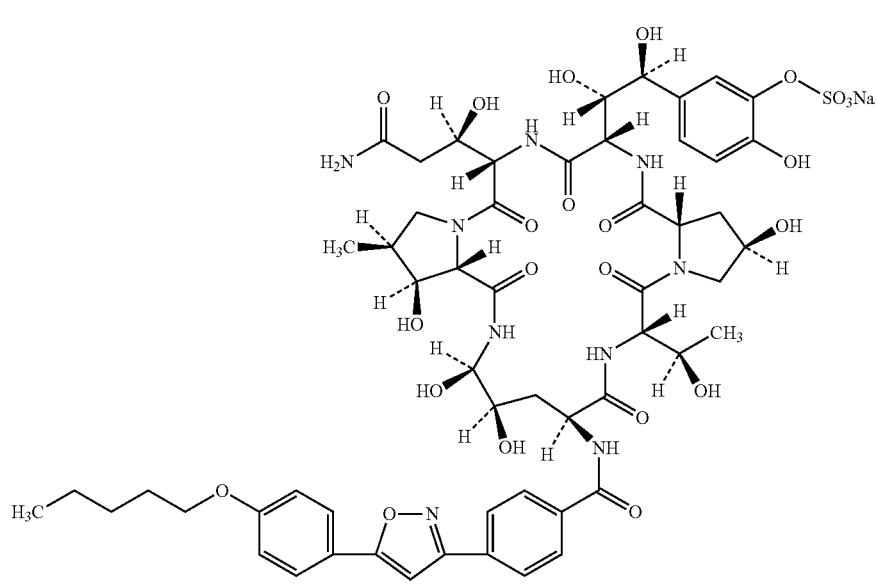

Sodium 5-[(1S,2S)-2-[(3S,6S,9S,11R,15S,18S,20R,21R,24S,25S,26S)-3-[(R)-2-carbamoyl-1-hy droxyethyl]-11,20,21,25-tetrahydroxy-15-[(R)-1-hydroxyethyl]-26-methyl-2,5,8,14,17,23-hexaoxo-18-[4-[5-(4-pentoxyphenyl)isoxazol-3-yl]benzoylamino]-1,4,7,13,16,22-hex aazatricyclo[22.3.0.0$^{9,13}$]heptacosan-6-yl]-1,2-dihydroxyethyl]-2-hydroxy phenyl sulfate.

The compound of formula I is a polypeptide compound with poor stability, and its quality and efficacy will be affected by degraded products generated during transportation or long-term preservation. And it is difficult to crystallize the compound of formula I, and generally, it is amorphous.

U.S. Pat. Nos. 6,107,458 and 7,199,248 and WO 96/111210 disclosed methods for preparing and purifying the compounds of Formula I. Wherein, in U.S. Pat. No. 7,199,248, Micafungin DIPEA (diisopropylethylamine) salt was purified through filtration and chromatographic separation, and then precipitated with acetone and ethyl acetate to give the amorphous form of the compound of formula I.

In Atsushi Ohigashi et al., "Process Development of Micafungin, a Novel Lipopeptide Antifungal Agent", *Journal of Synthesit Organic Chemistry*, 2006, Vol 64, 12, it was disclosed that the compound of formula I can be precipitated by adding a mixture of acetone and ethyl acetate to the elution solution of the compound of formula I from ion exchange, so as to give the amorphous compound of formula I. Before drying, the content of solvent in the precipitate of the compound of formula I was high (Dry/Wet=0.25), and about 75% of solvent is contained in the precipitate of the compound of formula I. For reducing the content of solvent below the standard, the drying time has to be extended. However, the extension of drying time will result in an increase in the degraded products of the compound of formula I and reduction in the quality.

In addition, the patent application WO 03/018615 of Fujisawa Pharmaceutical Co., Ltd. disclosed a new crystal form of the compound of the formula I and a preparation method thereof. In WO03/018615, the compound of formula I in amorphous form was dissolved in an aqueous single alcohol solution or aqueous acetone solution, and a solvent, such as ethyl acetate, methylene chloride, acetone and acetonitrile was added, so as to give needle-like crystals of the compound of formula I of B82 type. The crystal was obtained in an organic solvent, showed needle-like under microscope, and has peaks at the following 2θ angles in the X-ray diffraction pattern: 4.60, 5.4°, 9.0°, 9.8°, 16.9°.

YAMASHITA et al., from Fujisawa Pharmaceutical Co., Ltd. disclosed ("Study of Industrial Manufacturing Methods for Micafungin (FK463)", *Seibutsu kogaku Kaishi*, 2005, Vol 83) that needle-like crystals of FK463 were successfully obtained through optimization of solvent and control of pH, however, no specific embodiments and crystal data were disclosed. Since the prior patent application WO03/018615 of the company disclosed B82-type needle-like crystals of the compounds of formula I, it is assumed that YAMASHITA et al. also obtained needle-like crystals of B82 type.

The present inventors prepared needle-like crystals of B82 type according to the method of Example 1 in WO03/018615, and the obtained crystal was observed under an optical microscope, which is about 1 μm in size and a fine needle-like crystal. When the crystals are subjected to subsequent steps, such as filtration, drying or the like, the present inventors found that it is difficult to filter the crystals of the compound of formula I since the crystals of B82 type are in a fine needle-like form, and the operation time is long; before drying the crystals, the content of solvent in the compound of formula I (Dry/Wet) was about 0.25, and a large amount of organic solvent are contained in the crystals. The content of solvent has to be in line with API requirements by increasing the drying temperature or drying time during the drying process. However, such drying process will increase the degraded product of the compound of formula I, seriously affecting the quality and stability of API.

At present, it is disclosed that solids of Micafungin sodium are of poor stability, and can only be stored at a low temperature or a large amount of excipients have to be added to ensure its stability, which greatly limits the development of pharmaceutical uses of Micafungin sodium. If a stable solid of Micafungin sodium can be found, it can be prepared into various different formulations, such as freeze-dried powder, tablets, capsules, ointment, etc., to facilitate the use for different patients.

Therefore, there is an urgent need in the art to obtain a stable form of the compound of formula I with better stability, thereby achieving better commercial production.

SUMMARY OF THE INVENTION

One object of the present invention is to provide a solvate of the compound of formula I.

Another object of the present invention is to provide preparation methods for the solvate.

Another object of the present invention is to provide uses of the solvate.

Solvate of the Compound of Formula I

In the present invention, a solvate of the compound of formula I is provided, and 1 molecule of the solvate of the compound of formula I comprises 2 molecules of crystalline water and 0.5 molecule of methanol.

In another preferred embodiment of the present invention, the solvate of the compound of formula I has following characteristic peaks at the following 2θ angles in the X-ray diffraction pattern (XRPD): 3.6±0.2°, 6.4±0.2°, 6.8±0.2°, 9.5±0.2°.

In another preferred embodiment of the present invention, the solvate of the compound of formula I has other characteristic peaks at the following 2θ angles in the X-ray diffraction pattern (XRPD): 7.5±0.2°, 11±0.2°, 12.4±0.2°.

In another preferred embodiment of the present invention, the solvate of the compound of formula I has other characteristic peaks at the following 2θ angles in the X-ray diffraction pattern (XRPD): 13.4±0.2°, 20.2±0.2°.

In another preferred embodiment of the present invention, X-ray diffraction pattern (XRPD) of the solvate of the compound of formula I is shown in FIG. 1.

In another preferred embodiment of the present invention, the solvate of the compound of formula I has following parameters of crystal:

| Crystal system | Orthogonal | |
| --- | --- | --- |
| Space group | $P2_12_12_1$ | |

-continued

| Unit Cell | a = 11.8173(2) Å | α = 90° |
| --- | --- | --- |
| | b = 27.6924(5) Å | β = 90° |
| | c = 49.1479(8) Å | γ = 90° |
| Volume | 16083.6(5) Å$^3$ | Z = 8 |

Amorphous and crystalline form of the compound of formula I disclosed in the prior art have poor stability, and for obtaining the compound of formula I with better stability, the present inventors have studied the compound of formula I. Upon on study, it is found that: if only biphasic system is used, such as methanol/water, ethanol/water, n-propanol/water, isopropanol/water, isobutyl alcohol/water, n-butanol/water, acetonitrile/water, acetone/water, and the compound of formula I is precipitated by cooling and/or addition of an organic solvent, the precipitated solids were in amorphous form and of poor stability. In the further study, we have studied the content of water and the pH values for crystallization in the above two systems, however, finally, it is found that all of the obtained products were in amorphous form.

For obtaining the compound of formula I with good stability, the inventors did not abandon their efforts and continued to use different solvent combinations in a three-phase system to screen solvent systems. Upon a long period of research, the present inventors have unexpectedly found that a solvate of the compound of formula I, which is a column-like crystal with regular morphology, can be obtained in a specific three-phase solvent system. Afterwards, a large number of screening tests for solvent were carried out, and finally solvates of the compound of formula I with better stability and better morphology were obtained, and the preparation process was determined. Compared with the needle-like crystals of B82 type discloded in WO03/018615, the obtained solvate of the compound of formula I is a column-like crystal with regular morphology (FIG. 12), of large particle size and easy to be filtered the solvent in the crystal can be easily removed, and, more importantly, the stability thereof is better than that of the crystal of B82 type. Solvent-free crystals of the compound of formula I can be formed by removing solvents in the solvate of the compound of formula I.

The inventors further investigated the structure of the solvate of the compound of formula I and found that the water molecule and the methanol molecule bind with the sodium atom in the compound of formula I to form a eutectic composition, wherein one molecule of the solvate of the compound of formula I comprises 2 molecules of crystalline water and 0.5 molecule of methanol. Moreover, the solvate may also comprise free (unbound with the molecule of the compound of formula I) solvent or water, because during the preparation of solvates through crystallization of a compound, molecules of the compound form solvates of stable structure with molecules of solvent or molecules of water for crystallization, however, a certain amount of molecules of solvent or water will be wrapped or adsorbed between the molecules of the compound, these molecules of solvent and water do not bind with the molecules of the compound, and therefore do not participate in the formation of structure. The content and presence of such molecules of solvent and water do not affect the structure, and contents thereof will be uncertain.

Identification and Properties of the Solvate of the Compound of Formula I

After obtaining the solvate of the compound of formula I, the present inventors have further studied properties of the solvate by using various means and instruments.

At present, X-ray powder diffraction, i.e., X-ray polycrystal diffraction (XRD or XRPD), is commonly used as the test method for determining the structure of crystal (i.e., crystal form). X-ray powder diffractometer is used, and a series of diffraction patterns can be produced when X-ray passing through a crystal. In the pattern, different diffraction lines and the intensities thereof are determined by atomic cluster having certain structure, thereby determining the structure of a crystal. The methods for determining the X-ray diffraction pattern of a crystal are known in the art. For example, X-ray diffraction pattern can be obtained by using RIGAKU D/max 2550VB/PC X-ray powder diffractometer with the scanning rate of 2°/min. Copper irradiated target is used.

The solvate of the compound of formula I according to the present invention possesses a unique crystal form, and there are specific characteristic peaks in the X-ray diffraction pattern. Particularly, the solvate of the compound of formula I according to the present invention possesses characteristic peaks at the following 2θ angles in the X-ray powder diffraction pattern: 3.6±0.2°, 6.4±0.2°, 6.8±0.2°, 9.5±0.2°; in a preferred embodiment, there are other characteristic peaks at the following 2θ angles in the pattern: 7.5±0.20, 11±0.2°, 12.4±0.2°; in another preferred embodiment, there are other characteristic peaks at the following 2θ angles in the pattern: 13.4±0.2°, 20.2±0.2°. More preferably, X-ray diffraction pattern (XRPD) of the solvate of the compound of formula I is substantially identical with FIG. 1.

"Single Crystal X-ray Diffraction Analysis (SXRD)" is a direct, independent, accurate, quantitative method for determining the crystal form of a drug, and is also a currently internationally recognized authoritative method for studying polymorphism of solid chemical drugs. The solvate of the compound of formula I according to the present invention was detected by Bruker single crystal diffractometer (German, SMART APEX-II (DUO)) at a temperature of 140(2)K ($\lambda$=1.54178 Å), and data were collected. The crystal size of the solvate used in the single crystal detection is 0.230× 0.080×0.030 mm.

According to the data of single crystal X-ray diffraction, the structure of the solvate of the compound of formula I was resolved, and it is found that, in the solvate of the compound of formula I, 2 molecules of the compound of formula I bind with 1 molecule of methanol, and 1 molecules of the compound of formula I bind with 2 molecules of water. And the solvate possesses following crystallographic parameters:

| | |
|---|---|
| Space group | P 21 21 21 |
| a, Å | 11.8173(2) |
| b, Å | 27.6924(5) |
| c, Å | 49.1479(8) |
| α | 90° |
| β | 90° |
| γ | 90° |
| Z (mplecule/Unit cell) | 8 |
| Volume, Å$^3$ | 16083.6(5) |
| Calculated density (Mg/m$^3$) | 1.330 |
| Molecular formula | C56.5H76N9O25.5NaS |

According to the above data, in the unit cell, 1 molecule of the solvate of the compound of formula I comprises ½ molecule of methanol and 2 molecules of water.

Additionally, the unit cell stacking diagram of the solvate of the compound of formula I shown in FIG. 4 was resolved by the inventors, and it is found that certain free isobutanol and water used in the process of crystallization is comprised in the diagram.

The content of water in the composition of the compound of formula I is determined by a detection method commonly known in the art. For example, the water content is determined by Karl Fischer (KF).

Gas chromatography (GC) used to seperate and detect trace impurities in a compound is an accurate, qualitative and quantitative method of analysis. In the present invention, the content of methanol in solvent-free crystals of the compound of formula I, which is prepared by using the solvate of the compound of formula I prepared in the present invention as the raw material, is determined by gas chromatography (GC), for determining whether methanol is efficiently removed.

High performance liquid chromatography (HPLC) is a common method for detecting the purity of a compound, wherein a liquid is used as the mobile phase and a high-pressure transfusion system is used for pumping the mobile phase, such as single solvents with different polarities or a mixture of solvents at different proportions, buffers, into a column packed with a stationary phase. Each component is separated in the column, and then enters into a detector for detection, thereby analyzing a sample. In the present invention, HPLC is used for determining the purity of the compound of formula I and studying the stability of a sample.

HPLC detection method is listed as follows:

Analysis Column: YMC-ODS 250×4.6 mm, 5 μm;

Mobile phase: acetonitrile:phosphate buffer (pH 3.0)=45:70;

Flow rate: 1 ml/min;

Column temperature: 35° C.;

Diluent: aqueous phosphate buffer;

Detection wavelength: 210 nm;

Injection volume: 10 μl.

Preparation of Solvate of the Compound of Formula I

A method for preparing the solvates of the compound of formula I is provided in the present invention.

During the course of study, the inventors have not only screened solvent system, but also studied the effect of pH on the solvate of the compound of formula I. A large number of experiments have shown that pH is not a decisive factor in obtaining the solvate of the compound of formula I. When a two-phase or three-phase solvent system is used in crystallization, the compound of formula I in amorphous form is obtained, and even if the pH is changed, solids in amorphous form are still obtained. However, after the solvate of the compound of formula I is obtained by using a three-phase solvent system in crystallization, even if the pH is changed, the solvate of the compound of formula I can still be obtained, as long as the compound of formula I can remain stable.

Finally, the inventors have determined the following methods for obtaining the solvate of the compound of formula I, including the steps of:

(a) dissolving the compound of formula I in an aqueous mixed solution of alcohols;

(b) obtaining the solvate by reducing the temperature and/or adding an organic solvent (i).

Wherein the mixed solution of alcohols in step (a) is selected from a group consisting of methanol/isobutanol, methanol/isopropanol, methanol/n-propanol.

Wherein, in the aqueous mixed solution of alcohols in step (a), the volume ratio of the two alcohols is 0.01-100, preferably 0.05-20, more preferably 0.1-10.

Wherein, in the aqueous mixed solution of alcohols in step (a), the ratio of total volume of the alcohol to the volume of water is 0.1 to 100, preferably 0.5 to 10, more preferably 1 to 7.

Wherein, the temperature for dissolution in step (a) is 10-50° C., preferably, 20-40° C.

Wherein, in step (a), 1-500 mg/ml, preferably 5-100 mg/ml, more preferably 10-50 mg/ml of the compound of formula I is contained, based on the total volume of the solution.

Wherein, in step (b), the organic solvent (i) is selected from a group consisting of n-propanol, isopropanol, isobutanol, methyl acetate, ethyl acetate, n-propyl acetate, isopropyl acetate.

Wherein, in step (b), the temperature is reduced to −40 to 35° C., preferably −20 to 35° C., more preferably −10 to 30° C., most preferably −5 to 15° C.

Wherein the volume ratio of organic solvent (i) in step (b) to the aqueous mixed solution of alcohols in step (a) is 0.1 to 50, preferably 0.1 to 10, and more preferably 1-5.

wherein, "vacuum-drying the solvate of the compound of formula I together with a water system" means that the solvate of the compound of formula I will be placed in a position where a sample is generally put in a vacuum-dryer, and an open container comprising the substance capable of releasing water vapor is placed around the solvate of the compound of formula I.

The solvate of the compound of formula I provided in the present invention also can be directly used in the preparation of medicaments for treating fungal infections.

A pharmaceutical composition comprising the solvate of the compound of formula I and a pharmaceutically acceptable carrier is also provided in the present invention.

Relevant Terms

As used herein, the term "the solvate of the compound of formula I", also named as "the solvate of compound I", means a substance formed through interaction of hydrogen bond, salt bond between the compound of formula I and organic solvents or water.

As used herein, the term "crystal" means the solid of a molecule or atom complex showing specific arrangement.

As used herein, "the compound of formula I", "compound I" and "the compound according to formula I" can be interchangeably used, all of which mean a compound of the following structural formula:

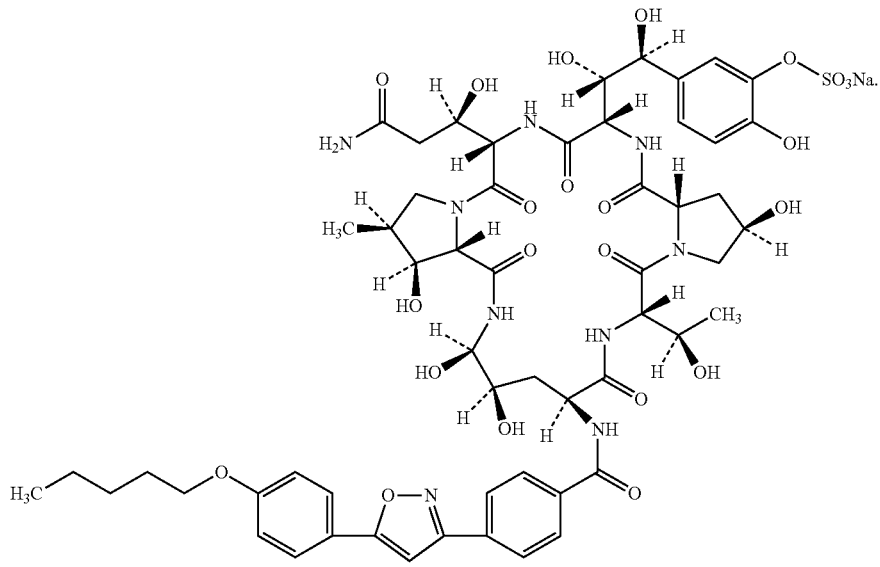

Formula I

Uses of the Solvate of the Compound of Formula I and Composition Thereof

The solvate of the compound of formula I provided in the present invention can be used to prepare the solvent-free crystal of the compound of formula I.

The method for preparing the solvent-free crystal of the compound of formula I from the solvate of the compound of formula I provided in the present invention includes the step of:

vacuum-drying the solvate of the compound of formula I provided in the present invention together with a water system, thereby obtaining the solvent-free crystal of the compound of formula I.

Wherein the water system includes tap water, pure water, ice-water mixture or other substance capable of releasing water vapor.

The compound of formula I can be obtained by routine methods in the art, for example (but not limited to), the preparation method disclosed in WO96/11210; alternatively, the compound can be commercially obtained, such as from Fujisawa, Japan.

As used herein, the term "pharmaceutically acceptable carrier" means the carriers that can be used to administrate therapeutics, including various excipients and diluents. The term means the drug carriers which themselves are not necessary active ingredients, and will not produce undue toxicity upon administration. Suitable carriers are generally known to the skilled in the art. Detailed review regarding the pharmaceutical acceptable excipient can be found in Remington's Pharmaceutical Sciences (Mack Pub. Co., N.J. 1991). Pharmaceutically acceptable excipients in a composition may include liquid, such as water, saline, glycol and ethanol. Additionally, auxiliary substances, such as disintegrating agents, wetting agents, emulsifying agents, pH buffering substances, etc., can be present in the carriers.

The advantages of the invention mainly include:

1. Solvates of the compound of formula I with superior stability were provided, which are convenient for transportation and storage, thereby resolving technical problems to be resolved in the prior art.

2. Preparation methods for the solvate of the compound of formula I are provided, and such methods are suitable for large-scale production.

BRIEF DESCRIPTION OF THE DRAWINGS

FIG. 1 shows the X-ray powder diffraction (XRPD) pattern of the solvate of the compound of formula I; wherein

| Number of peak | 2-θ | d (A) | I % (Relative Intensity) |
|---|---|---|---|
| 1 | 3.6 | 24.7974 | 100.0 |
| 2 | 6.4 | 13.7127 | 84.0 |
| 3 | 6.8 | 12.9885 | 42.9 |
| 4 | 7.5 | 11.7774 | 14.0 |
| 5 | 9.4 | 9.3605 | 42.8 |
| 6 | 10.8 | 8.1551 | 15.5 |
| 7 | 12.4 | 7.1206 | 15.8 |
| 8 | 13.6 | 6.5156 | 16.7 |
| 9 | 20.4 | 4.3580 | 24.6 |

Figure 2:
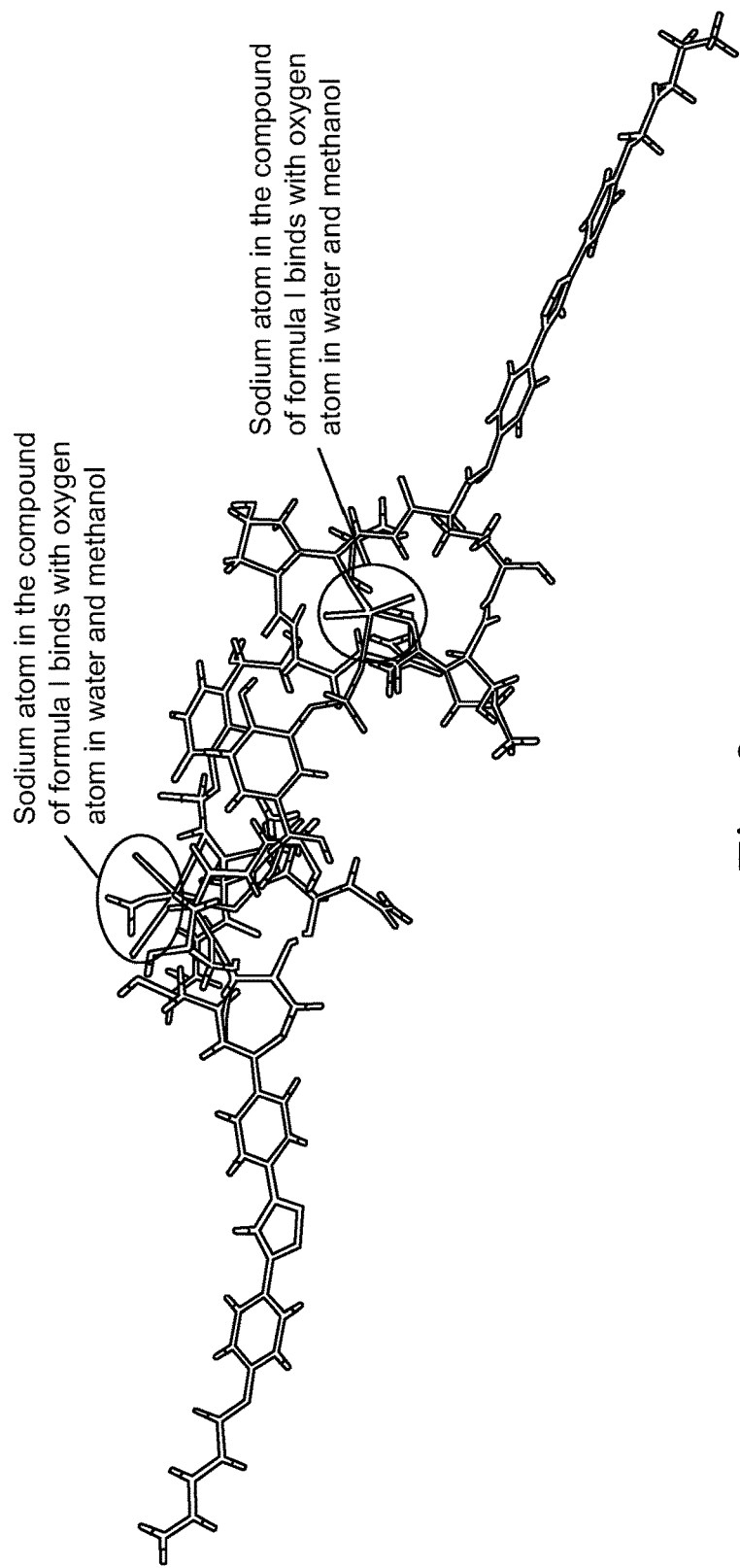

FIG. 2 shows the single crystal structure of the solvate of the compound of formula I.

Figure 3:
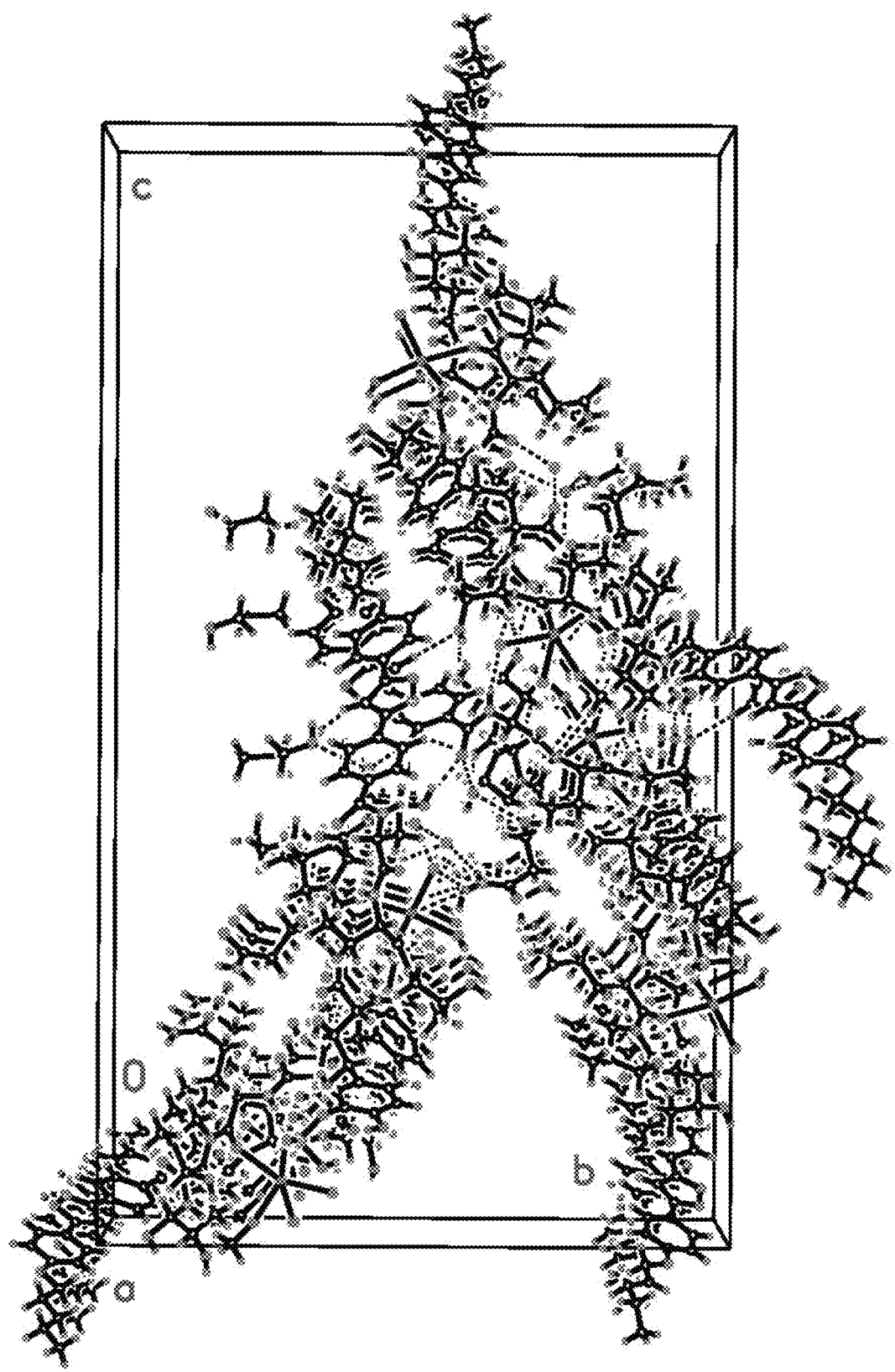

FIG. 3 shows the unit cell stacking diagram of the solvate of the compound of formula I.

Figure 4:
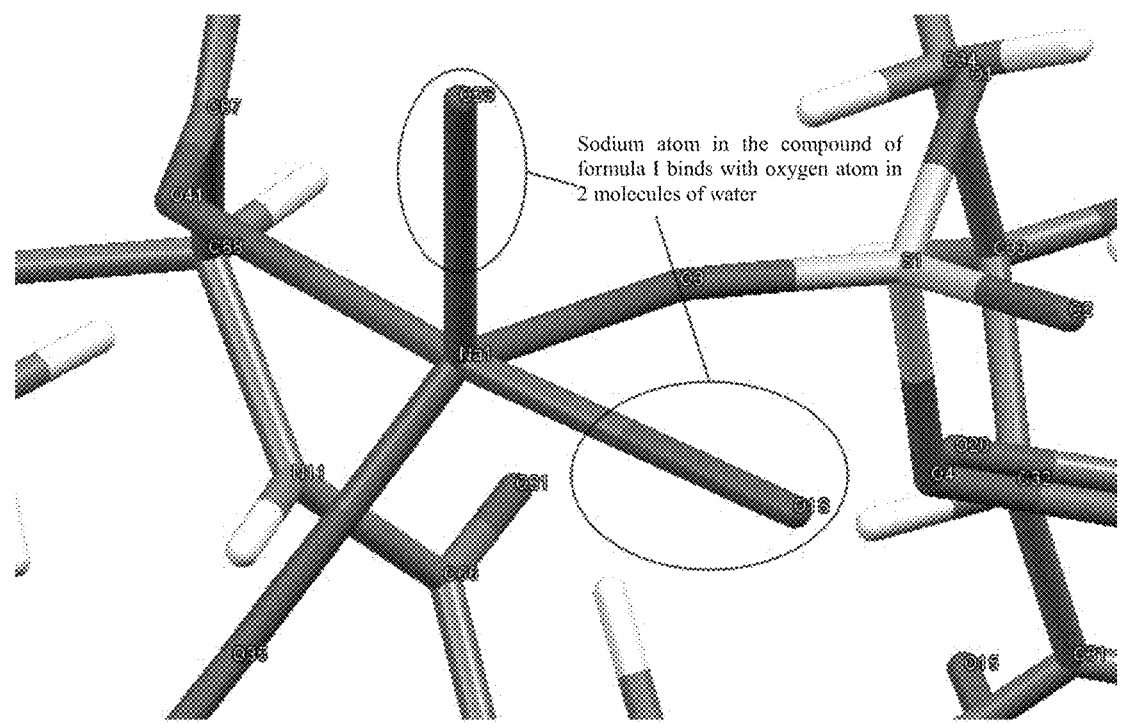

FIG. 4 shows a partial enlarged view of the single crystal structure of the solvate of the compound of formula I.

Figure 5:
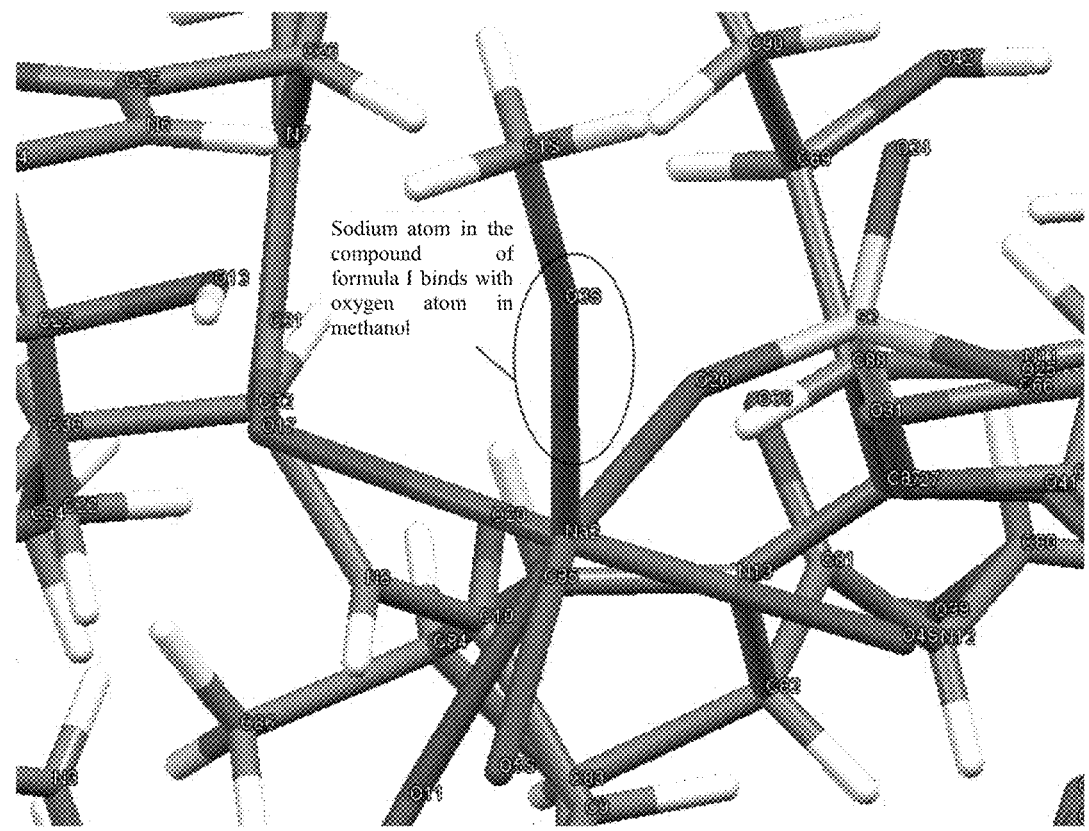

FIG. 5 shows a partial enlarged view of the single crystal structure of the solvate of the compound of formula I.

Figure 6:
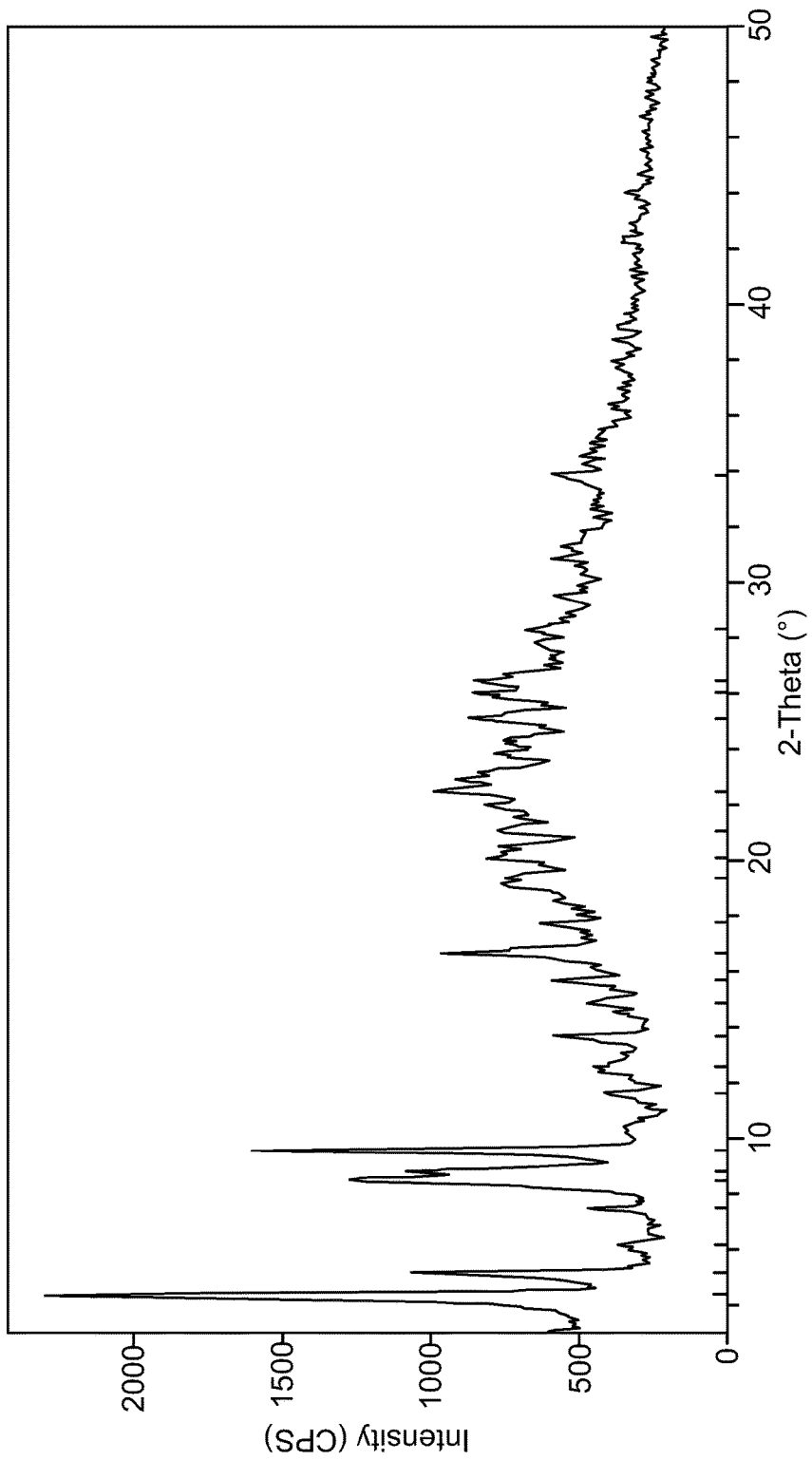

FIG. 6 shows the X-ray powder diffraction (XRPD) pattern of the solvent-free solvate of the compound of formula I.

Figure 7:
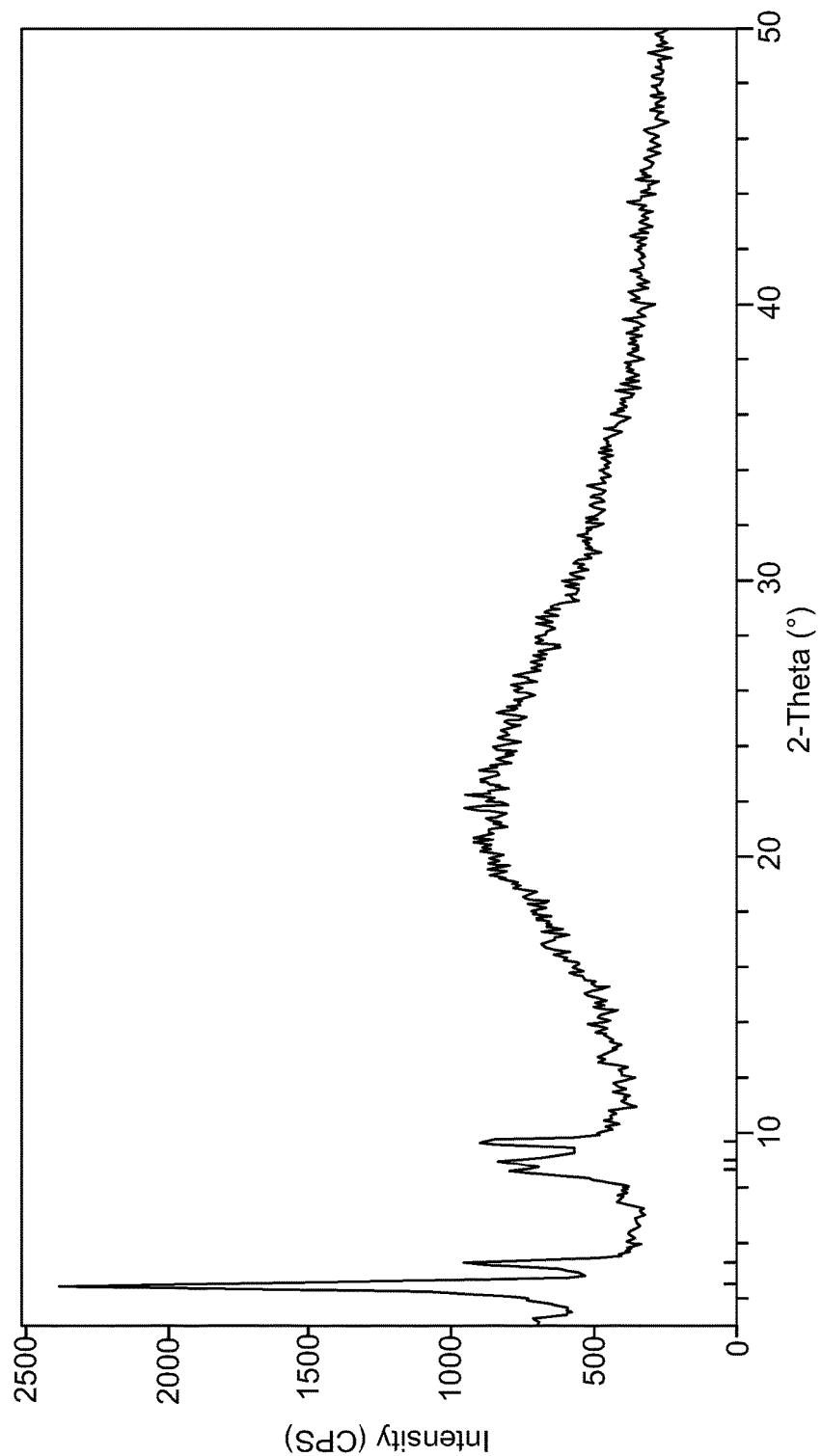

FIG. 7 shows the X-ray powder diffraction (XRPD) pattern of the solvent-free solvate of the compound of formula I.

Figure 8:
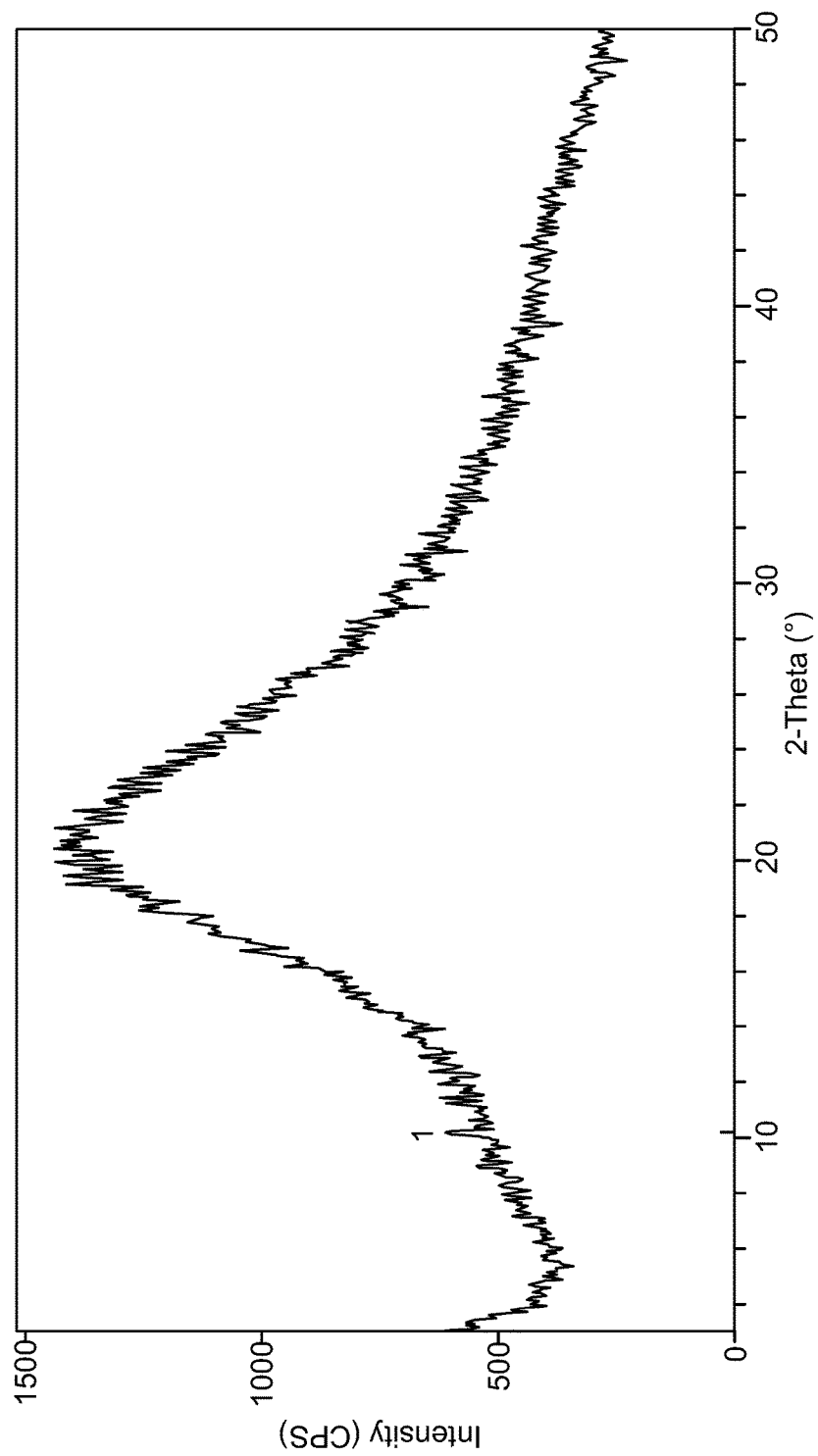

FIG. 8 shows the X-ray powder diffraction (XRPD) pattern of the compound of formula I in amorphous form.

Figure 9:
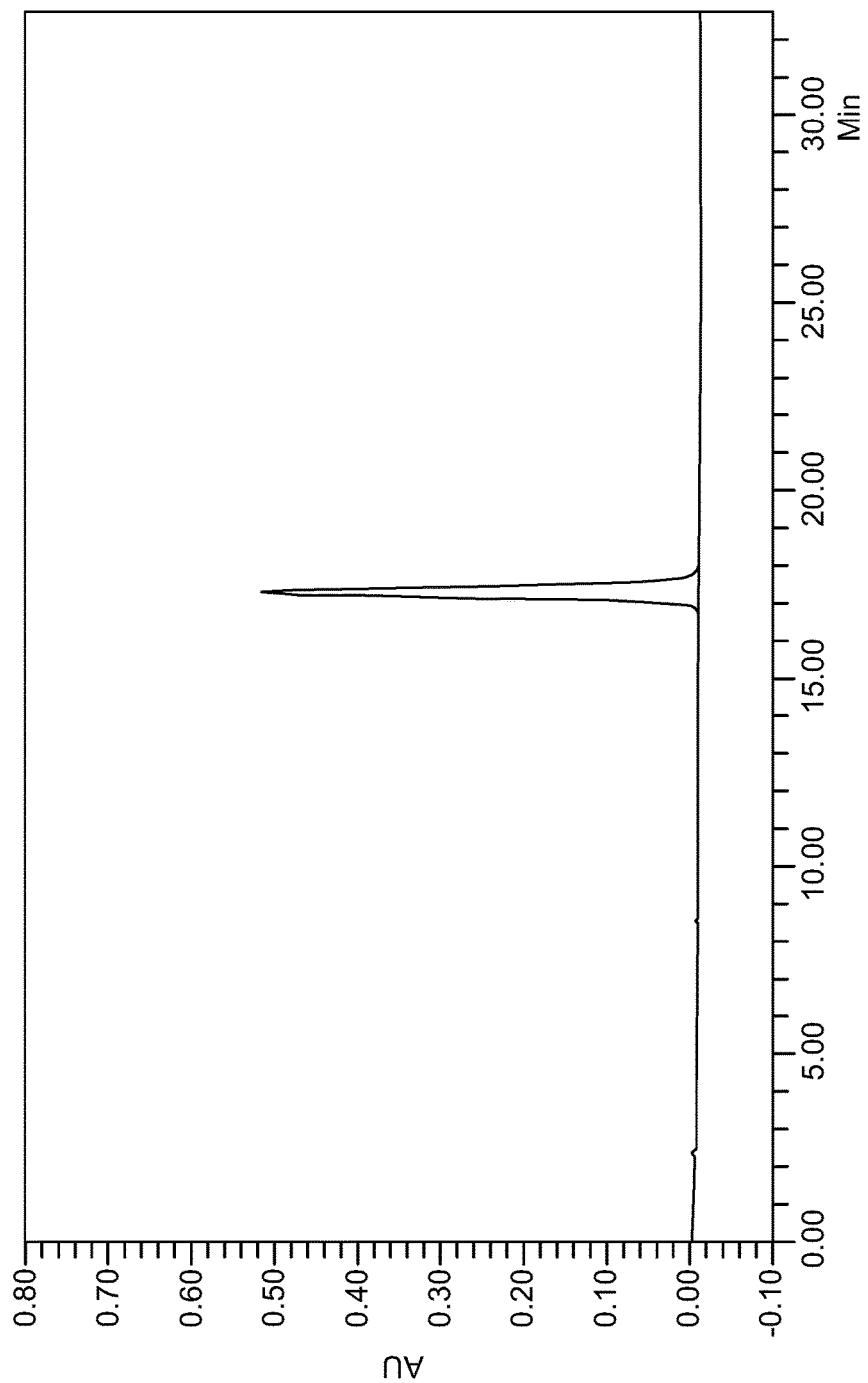

FIG. 9 is a HPLC pattern for the solvate of the compound of formula I obtained in Example 2 after placed at 25° C. for 30 days.

Figure 10:
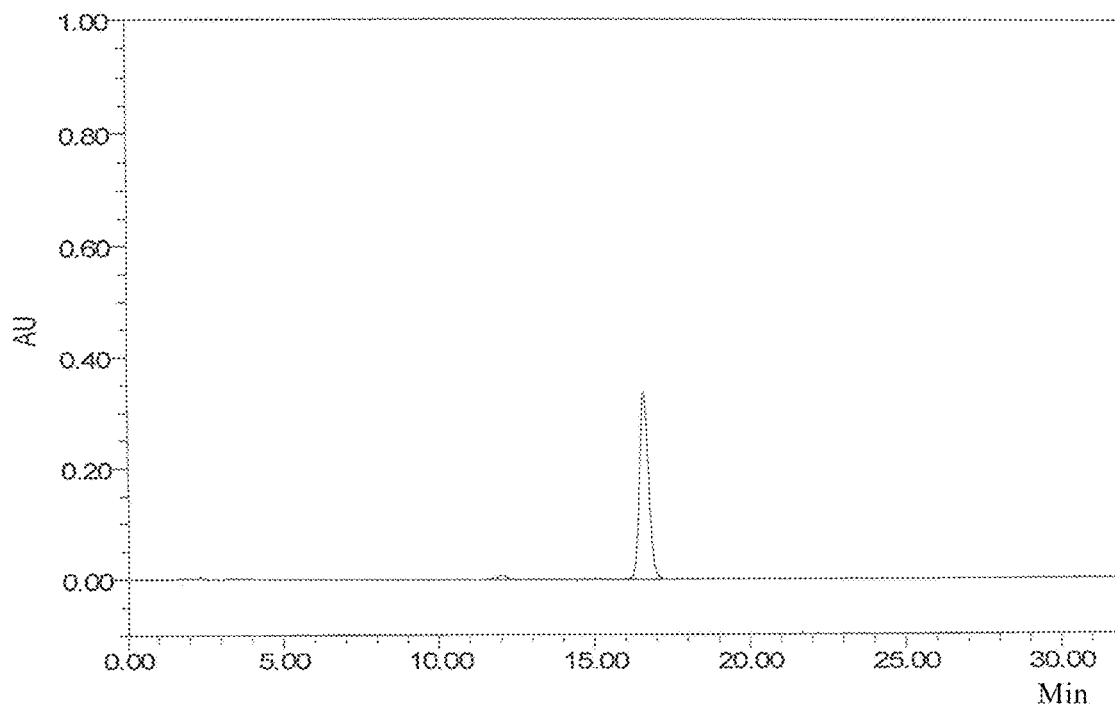

FIG. 10 is a HPLC pattern for crystal of B82 type obtained in Comparative Example 1 after placed at 25° C. for 30 days.

Figure 11:
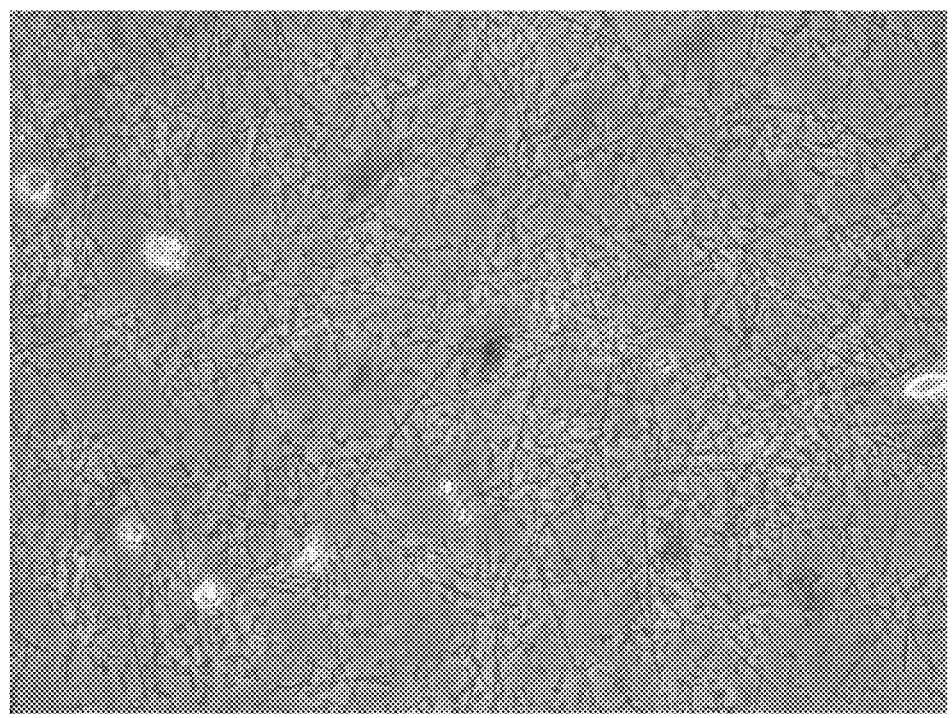

FIG. 11 shows a photograph of the crystal obtained in Comparative Example 1 observed under a microscope.

Figure 12:
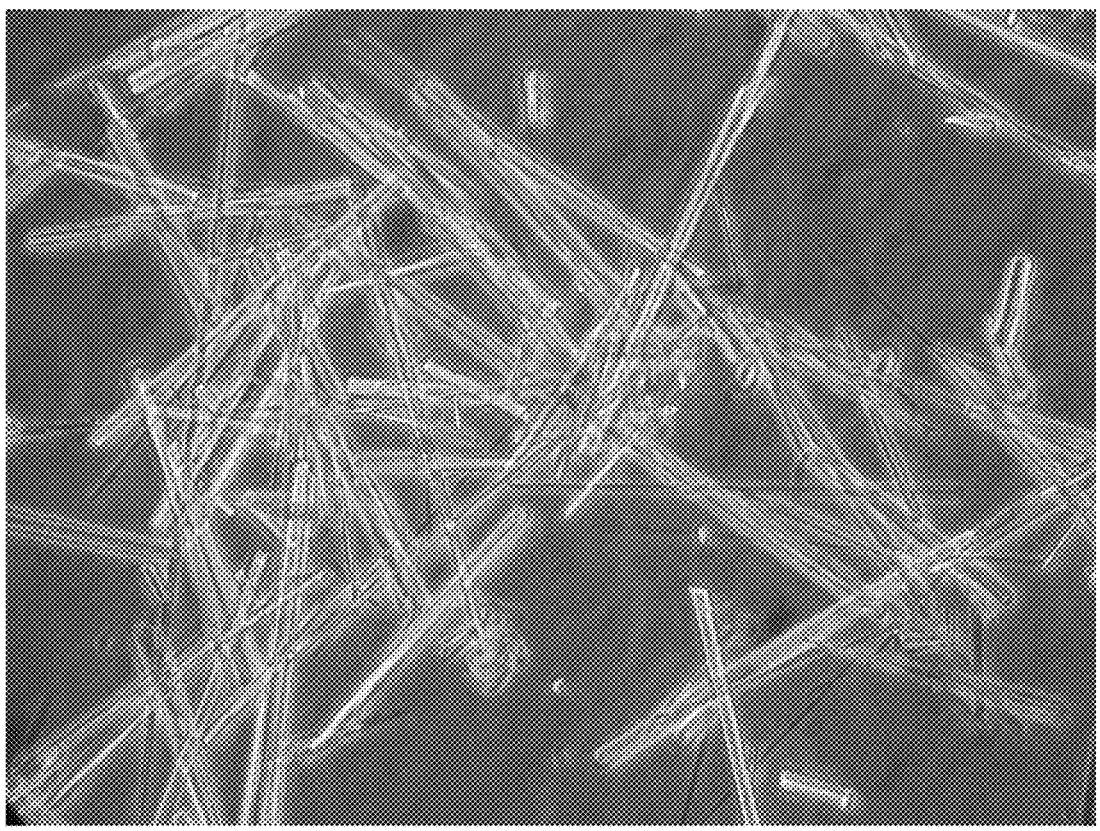

FIG. 12 shows a photograph of the crystal obtained in Example 2 observed under a microscope.

MODE FOR CARRYING OUT THE INVENTION

The invention will be further illustrated with reference to the following specific examples. It is to be understood that these examples are only intended to illustrate the invention, but not to limit the scope of the invention. For the experimental methods in the following examples without particular conditions, they are performed under routine conditions or as instructed by the manufacturer. Unless otherwise specified, all percentages, ratios, proportions or parts are by weight.

The unit of the weight/volume percentages in the invention is well known to the skilled in the art, for example, the weight of a solute in a 100 mL solution.

The content of water in a crystal is determined by a detection method commonly known in the art. For example, the water content is determined by Karl Fischer (KF).

Unless otherwise defined, all scientific and technical terms used herein have the same meaning as commonly understood by the skilled in the art. Furthermore, any process or material similar or equivalent to those described herein can be used in the process of the present invention. The preferred embodiments and materials described herein are merely provided for illustration.

Comparative Example 1

Preparation of the Crystal of B82 Type

Needle-like crystals, i.e., crystals of B82 type, were obtained according to the method of Examples 1-8 of WO03/018615. Crystals were taken before filtration and observed under a 15×40 microscope, and a photograph is shown in FIG. 11. B82 crystal is analyzed through single crystal X-ray diffraction, and it was confirmed that there was no solvent (methanol) and crystalline water in the unit cell, and the crystal belongs to non-solvate.

Example 1

Preparation of Compound I

The amorphous powder of the compound of formula I was prepared according to the method of U.S. Pat. No. 7,199,248, and the X-ray powder diffraction pattern thereof is shown in FIG. 8.

Example 2

Preparation of Solvate of the Compound of Formula I

At 25° C., 1 g of compound of formula I in amorphous form prepared in Example 1 was dissolved into 50 ml of aqueous methanol/isobutanol solution (isobutanol:water:methanol=8:2:1), the obtained solution was cooled to 8° C., crystals precipitated from the solution, and the system was stirred for 3.5 hours at this temperature, so that large amount of crystals precipitated. 90 ml of ethyl acetate was slowly added, and the crystals were sampled before filtration and observed under a microscope (15×40), photograph of which can be found in FIG. 12. The solvate of the compound of formula I was obtained by filtration, and XRPD pattern thereof can be found in FIG. 1.

Example 3

Preparation of Solvate of the Compound of Formula I

At 30° C., 2.5 g of crystals of B82 type prepared in Comparative Example 1 was dissolved into 50 ml of aqueous methanol/isobutanol solution (isobutanol:water:methanol=1:1:1), 50 ml of methyl acetate was slowly added, and the solvate of the compound of formula I was obtained by filtration.

Example 4

Preparation of Solvate of the Compound of Formula I

At 10° C., 3 g of compound of formula I in amorphous form prepared in Example 1 was dissolved into 600 ml of aqueous methanol/isobutanol solution (isobutanol:water:methanol=5:1:2), the obtained solution was cooled to −20° C., crystals precipitated from the solution, and the system was stirred for 12 hours, so that large amount of crystals precipitated. The solvate of the compound of formula I was obtained by filtration.

Example 5

Preparation of Solvate of the Compound of Formula I

At 50° C., 3 g of compound of formula I in amorphous form prepared in Example 1 was dissolved into 120 ml of aqueous methanol/isopropanol solution (isopropanol:water:methanol=4:2:1), the obtained solution was cooled to 30° C., crystals precipitated from the solution, and the system was stirred for 30 mins, so that large amount of crystals precipitated. 200 ml of isopropanol was slowly added, and the solvate of the compound of formula I was obtained by filtration.

Example 6

Preparation of Solvate of the Compound of Formula I

At 20° C., 1 g of compound of formula I in amorphous form prepared in Example 1 was dissolved into 20 ml of aqueous methanol/isopropanol solution (isopropanol:water:methanol=10:2:1), 200 ml of n-propyl acetate was slowly added, and the solvate of the compound of formula I was obtained by filtration.

Example 7

Preparation of Solvate of the Compound of Formula I

At 18° C., 1.0 g of compound of formula I in amorphous form prepared in Example 1 was dissolved into 100 ml of aqueous methanol/isopropanol solution (isopropanol:water:methanol=1:2:20), the obtained solution was cooled to −5° C., crystals precipitated from the solution, and the system was stirred for 4 hours, so that large amount of crystals precipitated. And the solvate of the compound of formula I was obtained by filtration.

Example 8

Preparation of Solvate of the Compound of Formula I

At 30° C., 2 g of compound of formula I in amorphous form prepared in Example 1 was dissolved into 20 ml of aqueous methanol/n-propanol solution (n-propanol:water:methanol=1:15:10), the obtained solution was cooled to 15° C., crystals precipitated from the solution, and the system was stirred for 2 hours, so that large amount of crystals precipitated. 200 ml of isopropyl acetate was slowly added, and the solvate of the compound of formula I was obtained by filtration.

Example 9

Preparation of Solvate of the Compound of Formula I

At 25° C., 4 g of compound of formula I in amorphous form prepared in Example 1 was dissolved into 300 ml of aqueous methanol/n-propanol solution (n-propanol:water:methanol=20:2:1), 30 ml of isobutanol was slowly added, and the solvate of the compound of formula I was obtained by filtration.

Example 10

Preparation of Solvate of the Compound of Formula I

At 40° C., 2.7 g of compound of formula I in amorphous form prepared in Example 1 was dissolved into 80 ml of aqueous methanol/n-propanol solution (n-propanol:water:methanol=10:3:1), the obtained solution was cooled to −10° C., crystals precipitated from the solution, and the system was stirred for 1 hour, so that large amount of crystals precipitated. And the solvate of the compound of formula I was obtained by filtration.

Example 11

Preparation of Solvate of the Compound of Formula I

At 25° C., 1 g of compound of formula I in amorphous form prepared in Example 1 was dissolved into 50 ml of aqueous isobutanol/methanol solution (isobutanol:water:methanol=8:2:1), the obtained solution was cooled to about 5° C. for about 60 hours, and the solvate of the compound of formula I was obtained. Upon single crystal X-ray diffraction analysis, it was confirmed that 1 molecule of the compound of formula I, ½ molecule of methanol and 2 molecules of water were contained in the unit cell. The crystal structure of the solvate can be found in FIG. 2, and the unit cell stacking diagram can be found in FIG. 3.

Example 12

Preparation of Solvent-Free Crystal of the Compound of Formula I

At 20° C., 1.5 g of compound of formula I in amorphous form prepared in Example 1 was dissolved into 70 ml of aqueous methanol/isobutanol solution (isobutanol:water:methanol=8:2:1), the obtained solution was slowly cooled to 0° C., crystals precipitated from the solution, and the system was stirred for 4.5 hours at this temperature, so that large amount of crystals precipitated. 100 ml of ethyl acetate was slowly added, and the solvate of the compound of formula I was obtained by filtration. The obtained solvate was placed into a vaccum-drying oven, a plate of pure water was put on the bottom of the vacuum-dryer, and the content of water was controlled at 7.9%. The solvent-free crystal of the compound of formula I was obtained by vaccum-drying, and the XRPD pattern thereof can be found in FIG. 6. And no methanol or other organic solvents were detected by GC.

Example 13

Preparation of Solvent-Free Crystal of the Compound of Formula I

At 27° C., 2 g of compound of formula I in amorphous form prepared in Example 1 was dissolved into 100 ml of aqueous methanol/isobutanol solution (isobutanol:water:methanol=8:2:1), the obtained solution was slowly cooled to −20° C., crystals precipitated from the solution, and the system was stirred for 4 hours at this temperature, so that large amount of crystals precipitated. 150 ml of ethyl acetate was slowly added, and the solvate of the compound of formula I was obtained by filtration. The obtained solvate was placed into a vaccum-drying oven, a plate of tap water was put on the bottom of the vacuum-dryer, and dried for 16 hours. The tap water was removed, the solvate was continually vaccum-dried, and the content of water was controlled at 3.7%. The solvent-free crystal of the compound of formula I was obtained, and the XRPD pattern thereof can be found in FIG. 7. And no methanol or other organic solvents were detected by GC.

Comparative Example 2

Effects of Different Solvents on the Crystal Forms of the Compound of Formula I

At 25° C., 0.4 g of compound of formula I in amorphous form prepared in Example 1 was dissolved into 10 ml of aqueous methanol solution (methanol:water=3:2). The obtained solution was slowly cooled to 5° C., crystals precipitated from the solution, and the system was stirred for 3 hours at this temperature. An amorphous powder was obtained by filtration.

Comparative Example 3

Effects of Different Solvents on the Crystal Forms of the Compound of Formula I

At 30° C., 2 g of compound of formula I in amorphous form prepared in Example 1 was dissolved into 10 ml of aqueous acetone solution (acetone:water=1:1). The obtained solution was slowly cooled to 5° C., solids precipitated from the solution, and the system was stirred for 4 hours at this temperature. 50 ml of ethyl acetate was slowly added, and an amorphous powder was obtained by filtration.

Comparative Example 4

Effects of Different Solvents on the Crystal Forms of the Compound of Formula I

At 30° C., 1.7 g of compound of formula I in amorphous form prepared in Example 1 was dissolved into 100 ml of aqueous methanol/ethanol solution (methanol:ethanol:water=8:2:1). The obtained solution was slowly cooled to 11° C., solids precipitated from the solution, and the system was stirred for 6 hours at this temperature. 100 ml of ethyl acetate was slowly added, and an amorphous powder was obtained by filtration.

Comparative Example 5

Effects of Different Solvents on the Crystal Forms of the Compound of Formula I

At 45° C., 4 g of compound of formula I in amorphous form prepared in Example 1 was dissolved into 28 ml of aqueous methanol/n-butanol solution (methanol:n-butanol:water=1:7:2). The obtained solution was slowly cooled to 11° C., solids precipitated from the solution, the system was stirred for 6 hours at this temperature, and an amorphous powder was obtained by filtration.

Comparative Example 6

Effects of Different Solvents on the Crystal Forms of the Compound of Formula I

At 50° C., 3 g of compound of formula I in amorphous form prepared in Example 1 was dissolved into 20 ml of aqueous methanol/ethanol solution (methanol:acetonitrile:water=4:1:2). The obtained solution was slowly cooled to 25° C., solids precipitated from the solution, the system was stirred for 2 hours at this temperature, 70 ml of ethyl acetate was slowly added, and an amorphous powder was obtained by filtration.

Example 14

Purity and Stability Test

In this Example, the purity and stability of samples obtained in Comparative Examples and Examples were compared. The used method is described as follows:

The solvate of the compound of formula I prepared in Examples 2, the crystal of B82 type obtained in Comparative Example 1 and amorphous solids obtained in Example 1 were taken and sealed at 25° C. for 30 days respectively. And then the content of impurities in the sample was analyzed. Results for comparing the stability of the solvate of the compound of formula I according to the present invention, the crystal of B82 type and the amorphous solid are shown in the following table:

| Sample | Purity of initial sample | Purity of sample after stored ar 25° C. for 30 days |
| --- | --- | --- |
| Solvate of the compound of formula I | 99.55% | 99.50% |
| Crystal of B82 type | 99.50% | 96.98% |
| Amorphous solids | 99.38% | 89.27% |

Example 15

Preparation of Pharmaceutical Composition

| Solvate of the compound of formula I | Lactose | Anhydrous citric acid | Sodium hydroxide |
| --- | --- | --- | --- |
| 2.5 g | 20 g | q.s. | q.s. |

20 g of lactose was dissolved in purified water (200 ml) by heating at less than 50° C. After cooling to 20° C. or lower, 2.5 g of the solvate of the compound of formula I obtained according to the method in Example 2 was added to the lactose solution, and gently agitated to avoid generation of bubbles. 2% aqueous citric acid solution (0.95 ml) was added, 0.4% aqueous sodium hydroxide solution (about 24 ml) was added to the solution to adjust pH 5.5, and then diluted with pure water to give a volume of 250 ml. The resulting solution was dispensed into 100 vials of 10 ml volume, 2.5 ml per vial. The solution in each vial was lyophilized through a conventional method using a lyophilizer to obtain a lyophilized composition, each containing 25 mg of the solvate of the compound of formula I.

Example 16

Preparation of Pharmaceutical Composition 0.2 g of the solvate of the compound of formula I obtained according to the method in Example 2 was taken and prepared into an eye drop according to the method in Example 2 of US2007249546A1.

Characterization of Solvate of the Compound of Formula I

Figure 1:
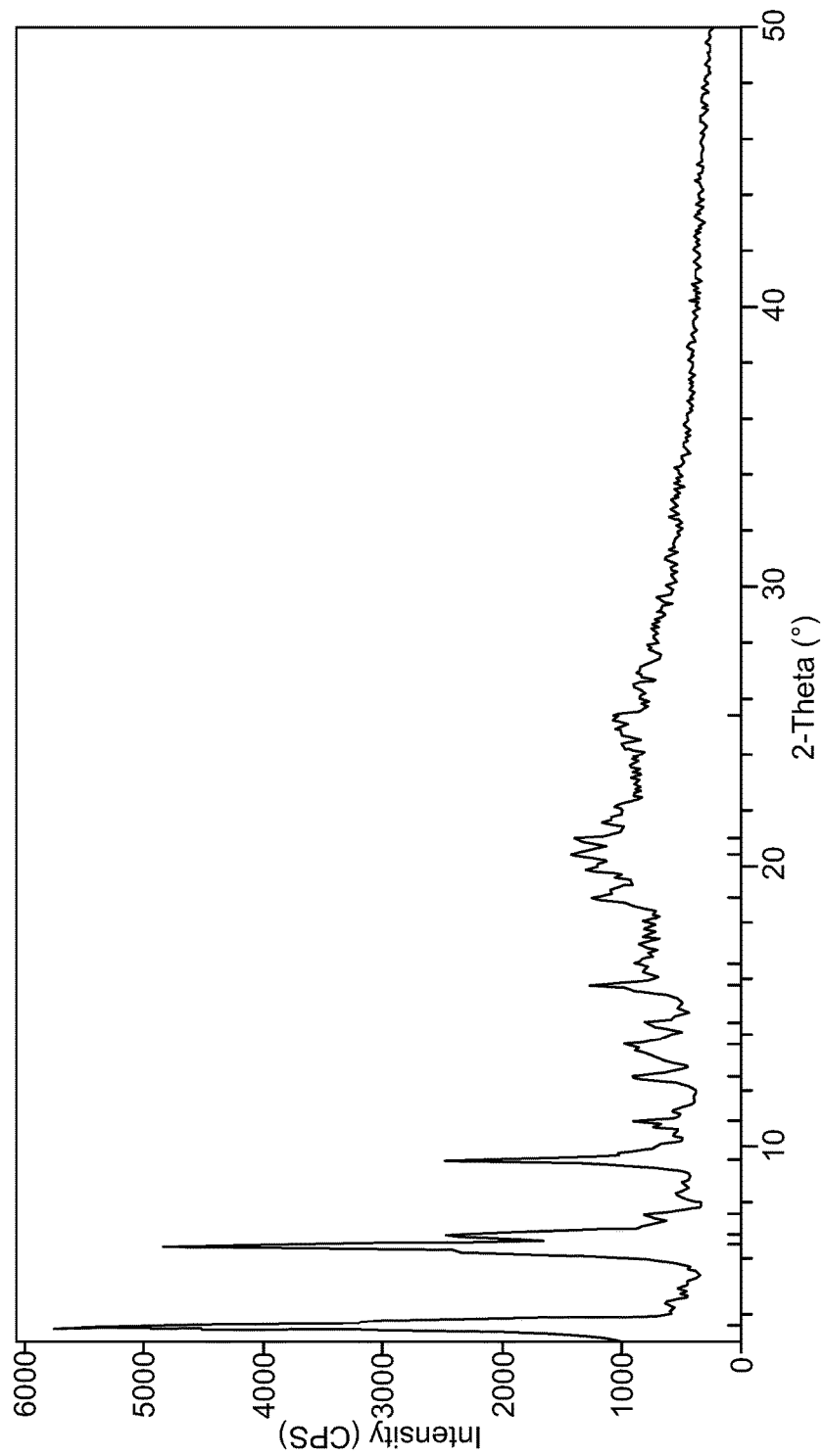

The solvate of the compound of formula I obtained in Example 2 was determined by X-ray powder diffractometer, there are characteristic peaks at the following 2θ angles in the X-ray diffraction pattern: 3.6±0.2°, 6.4±0.2°, 6.8±0.2°, 7.5±0.2°, 9.5±0.2°, 11.0±0.2°, 12.4±0.2°, 13.4±0.2°, 20.2±0.2°; and the X-ray diffraction pattern is shown in FIG. 1.

The single crystal structure of the solvate of the compound of formula I is shown in FIG. 2.

The unit cell stacking diagram of the solvate of the compound of formula I is shown in FIG. 3.

Upon determination, the structure of the crystals of Examples 3-11 is identical with that of the crystal of Example 2. Therefore, the reproducibility of the method of the present invention is excellent, and the solvate of the compound of formula I which is stable can be obtained.

The above mentioned embodiments are preferred embodiments of the present invention, and not provided to limit the scope of substantial technical contents of the present invention, which are broadly defined in the claims of the present application. If any technical entity or method completed by other people is identical with that defined by the claims of the present application, or is an equivalent modification, all of them will be deemed as falling within the scope of the claims.

The invention claimed is:

1. A solvate of the compound of formula I, wherein 1 molecule of the solvate of the compound of formula I comprises 2 molecules of crystalline water and 0.5 molecule of methanol;

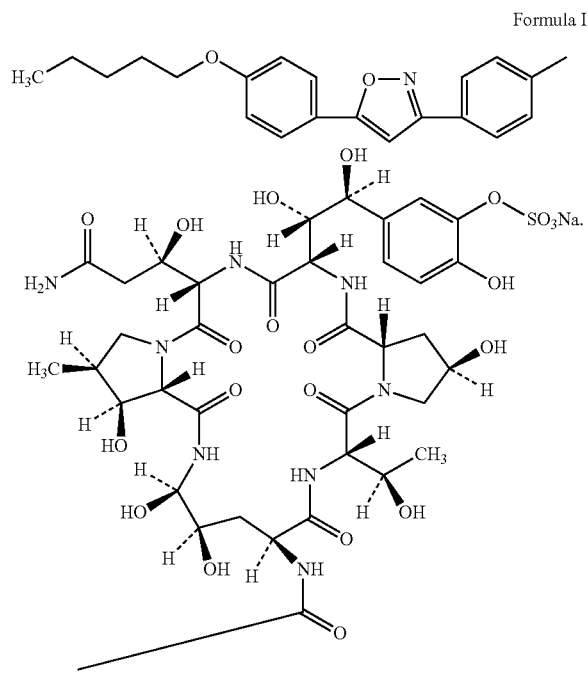

Formula I

2. The solvate of claim 1, wherein the solvate of the compound of formula I has following characteristic peaks at the following 2θ angles in the X-ray diffraction pattern (XRPD): 3.6±0.2°, 6.4±0.2°, 6.8±0.2°, 9.5±0.2°.

3. The solvate of claim 1, wherein the solvate also comprises a solvent or water used during the preparation, and the solvent or water exists in a free form.

4. A pharmaceutical composition comprising the solvate of claim 1 and a pharmaceutically acceptable carrier.

5. A method for preparing the solvate of claim 1, the method comprising the steps of:

(a) dissolving the compound of formula I in an aqueous mixed solution of alcohols, wherein the aqueous mixed solution of alcohols is selected from the group consisting of methanol/isobutanol, methanol/isopropanol, and methanol/n-propanol; and (b) obtaining the solvate of claim 1 by reducing the temperature and/or adding an organic solvent selected from the group consisting of n-propanol, isopropanol, isobutanol, methyl acetate, ethyl acetate, n-propyl acetate, and isopropyl acetate.

6. The method of claim 5, wherein, in the aqueous mixed solution of alcohols in step (a), the volume ratio of the two alcohols is 0.01-100.

7. The method of claim 5, wherein, in the aqueous mixed solution of alcohols in step (a), the ratio of total volume of the two alcohols to the volume of water is 0.1 to 100.

8. The method of claim 5, wherein, in step (b), the temperature is reduced to −40 to 35° C.

9. The method of claim 5, wherein the volume ratio of the organic solvent in step (b) to the aqueous mixed solution of alcohols in step (a) is 0.1 to 50.

10. The method of claim 6, wherein, in the aqueous mixed solution of alcohols in step (a), the volume ratio of the two alcohols is 0.05-20.

11. The method of claim 6, wherein, in the aqueous mixed solution of alcohols in step (a), the volume ratio of the two alcohols is 0.1-10.

12. The method of claim 7, wherein, in the aqueous mixed solution of alcohols in step (a), the ratio of total volume of the two alcohols to the volume of water is 0.5 to 10.

13. The method of claim 7, wherein, in the aqueous mixed solution of alcohols in step (a), the ratio of total volume of the two alcohols to the volume of water is 1 to 7.

14. The method of claim 8, wherein, in step (b), the temperature is reduced to −20 to 35° C.

15. The method of claim 8, wherein, in step (b), the temperature is reduced to −10 to 30° C.

16. The method of claim 8, wherein, in step (b), the temperature is reduced to −5 to 15° C.

17. The method of claim 9, wherein the volume ratio of the organic solvent in step (b) to the aqueous mixed solution of alcohols in step (a) is 0.1 to 10.

18. The method of claim 9, wherein the volume ratio of the organic solvent in step (b) to the aqueous mixed solution of alcohols in step (a) is 1 to 5.

19. A method for preparing a solvent-free crystal of the compound of formula I, the method comprising the step of:

vacuum-drying the solvate of the compound of formula I according to claim 1 together with a water system, thereby obtaining the solvent-free crystal.

20. The method of claim 19, wherein the water system is tap water, pure water, ice-water mixture, or a substance capable of releasing water vapor.

21. A method for treating fungal infections comprising administering to a subject in need thereof the solvate of the compound of formula I according to claim 1.

22. A method for preparing the pharmaceutical composition of claim 4, including the step of:

mixing the solvate of claim 1 and a pharmaceutically acceptable carrier, thereby obtaining the pharmaceutical composition of claim 4.

* * * * *